US00PP18846P2

(12) United States Plant Patent
Olsthoorn

(10) Patent No.: US PP18,846 P2
(45) Date of Patent: May 27, 2008

(54) *SPATHIPHYLLUM* PLANT NAMED 'SWEET SILVANA'

(50) Latin Name: *Spathiphyllum Schott*
Varietal Denomination: Sweet Silvana

(75) Inventor: Petrus C. M. Olsthoorn, Honselersdijk (NL)

(73) Assignee: P.C.M. Olsthoorn Holding BV, Honselersdijk (NL)

( * ) Notice: Subject to any disclaimer, the term of this patent is extended or adjusted under 35 U.S.C. 154(b) by 31 days.

(21) Appl. No.: 11/442,938

(22) Filed: May 30, 2006

(51) Int. Cl.
*A01H 5/00* (2006.01)

(52) U.S. Cl. ..... Plt./364

(58) Field of Classification Search ..... Plt./364
See application file for complete search history.

(56) References Cited

PUBLICATIONS

Upov Plant Variety Database CD–Room search for the cultivar Sweet Silvana, 1 page.*

* cited by examiner

*Primary Examiner*—Annette H Para

(57) ABSTRACT

A new cultivar of *Spathiphyllum* plant named 'Sweet Silvana' that is characterized by white to cream colored spathes, dark green leaves and a fast growth rate.

1 Drawing Sheet

Botanical classification: *Spathiphyllum Schott.*
Variety denomination: 'Sweet Silvana'.

BACKGROUND OF THE INVENTION

The present invention relates to a new and distinct cultivar of *Spathiphyllum* plant botanically known as *Spathiphyllum Schott.* and hereinafter referred to by the cultivar name 'Sweet Silvana'.

'Sweet Silvana' is a hybrid that originated from the hybridization of the female or seed parent a proprietary *Spathiphyllum Schott.* identified as 96251-55 (not patented) and the male or pollen parent a proprietary *Spathiphyllum Schott.* identified as 96099-50 (not patented). The cultivar 'Sweet Silvana' was selected by the inventor in September of 1999 as a single plant within the progeny of the stated cross in Honselersdijk, The Netherlands.

Asexual reproduction by tissue culture of the new cultivar 'Sweet Silvana' was first performed in 2000 in Honselersdjik, The Netherlands. Since that time, under careful observations, the unique characteristics of the new cultivar have been uniform, stable and reproduced true to type in successive generations of asexual reproduction.

SUMMARY OF THE INVENTION

The following represent the distinguishing characteristics of the new *Spathiphyllum* cultivar 'Sweet Silvana'.

1. *Spathiphyllum* 'Sweet Silvana' exhibits white to cream colored spathes.
2. *Spathiphyllum* 'Sweet Silvana' exhibits dark green leaves.
3. *Spathiphyllum* 'Sweet Silvana' exhibits a fast growth rate.

The closest comparison cultivar is *Spathiphyllum* 'Sweet Pablo' (U.S. Plant Pat. No. 10,817). The new cultivar 'Sweet Silvana' is distinguishable from 'Sweet Pablo' by the following characteristics:

1. 'Sweet Silvana' has flowers that are more cream colored. The flowers of 'Sweet Pablo' are white'.
2. 'Sweet Silvana' has a larger height than 'Sweet Pablo'.
3. 'Sweet Silvana' has darker green leaves than those of 'Sweet Pablo'.

The new cultivar 'Sweet Silvana' is distinguishable from the male parent *Spathiphyllum* '96099-50' in having narrower leaves. The new cultivar 'Sweet Silvana' is distinguishable from the female parent *Spathiphyllum* '96251-55' in having fewer leaves.

BRIEF DESCRIPTION OF THE DRAWING

The accompanying photograph illustrates the distinguishing traits of *Spathiphyllum* 'Sweet Silvana'. The plant in the photograph shows an overall view of a 47 week old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Spathiphyllum* cultivar named 'Sweet Silvana'. Data was collected in Honselersdijk, The Netherlands from 47 week old greenhouse grown plants in 17 cm containers. The time of year was Spring and the average temperature was 22 degrees Centigrade during the day and 20 degrees Centigrade at night. No photoperiodic treatments was used. 80–100 PPM of Gibberallic acid was applied for flower initiation. Color determinations are in accordance with The Royal Horticultural Society Colour Chart 2001 edition, except where general color terms of ordinary dictionary significance are used. The growing requirements are similar to the species. 'Sweet silvana' has not been tested under all possible conditions and phenotypic. differences may be observed with variations in environmental, climatic, and cultural conditions, however, without any variance in genotype.

Botanical classification: *Spathiphyllum Schott.* 'Sweet Silvana'.
Use: Ornamental.
Parentage: 'Sweet Silvana' is a hybrid plant that resulted from the hybridization of the following parent plants:
*Female parent.*—A proprietary *Spathiphyllum Schott.* identified as '96251-55'.
*Male parent.*—A proprietary *Spathiphyllum Schott.* identified as '96099-50'.
Vigor: Moderate.
Growth rate: Moderate.
Growth habit: Moderately branching from base, bushy and dense.
Plant shape: Inverted triangle with inflorescences on top.
Suitable container size: 17 cm diameter container.
Height: Average 62 cm to top of leaf plane, 78 cm to top of inflorescences.
Width: Average 62.5 cm in width.
Hardiness: USDA Zone 10.
Propagation: Tissue Culture.
Time to initiate roots (summer and winter): Approximately 14 days to produce roots on an initial cutting.
Time to produce a rooted cutting or liner (summer and winter): Approximately 39 days.
Root system: Fine and fibrous.
Stem: No stems, Leaves grow directly from base, Average 5 clumps, clump color 137A to 146A.
Foliage:
*Texture.*—Smooth with furrowed veins.
*Appearance.*—Glossy.
*Leaf arrangement.*—Alternate.
*Compound or single.*—Single.
*Leaf shape.*—Elliptic to narrow ovate.
*Leaf apex.*—Apiculate.
*Leaf base.*—Attenuate.
*Leaf length.*—Average 28.9 cm in length.
*Leaf width.*—12.4 cm in width.
*Quantity of leaves per clump.*—Average 7.
*Pubescence.*—Absent.
*Leaf margin.*—Entire, slightly wavy.
*Vein pattern.*—Pinnate.
*Young leaf color* (*upper surface*).—Between 141A and 143A.
*Young leaf color* (*lower surface*).—137A to 137B.
*Mature leaf color* (*upper surface*).—137A to 139A.
*Mature leaf color* (*lower surface*).—137B.
*Vein color* (*lower surface*).—144A to 144B.
*Vein color* (*upper surface*).—141A to 141B.
*Leaf attachment.*—Petiolate.
*Petiole dimensions.*—Average 25 cm in length excluding geniculum, 5 mm in diameter below geniculum to 12 mm in diameter above clump.
*Petiole aspect.*—Round.
*Petiole color.*—137A to 137C.
*Geniculum dimensions.*—Average 3.5 cm in length and 6.0 mm in diameter.
*Geniculum aspect.*—Rounded, dull, glabrous.
*Geniculum color.*—138B.
*Petiole sheath dimensions.*—Average 17.9 cm in length and 8 mm in diameter.
*Petiole sheath color.*—137A.
*Durability of foliage to stress.*—High.

Inflorescence:
*Inflorescence arrangement.*—Spathes with spadices held above the foliage on erect peduncles arising from the petiole sheath.
*Flowering habit.*—Continuous.
*Quantity of spathes per plant.*—Average 4.
*Natural flowering season.*—Autumn to winter.
*Time to flower or response.*—45 weeks.
*Fragrance.*—Moderate to strong, sweet.
*Self-cleaning or persistent.*—Persistent.
*Flower longevity.*—Lasts approximately 3 weeks on plant.
*Spathe aspect.*—Slightly cupped.
*Spathe dimensions.*—Average 21.1 cm in length, 8.5 cm in width and 1.7 cm in depth.
*Spathe texture.*—Glabrous, slightly leathery.
*Spathe shape.*—Ovate.
*Spathe margin.*—Entire, slightly wavy.
*Spathe apex.*—Apiculate.
*Spathe base.*—Cuneate.
*Spathe color when opening* (*front side*).—155C, main vein 143D.
*Spathe color when opening* (*back side*).—155C, main vein 143C to 143B.
*Spathe color when fully opened* (*front side*).—155C, main vein 143D.
*Spathe color when fully opened* (*back side*).—155C, main vein 143B.
*Spathe color fading to.*—Not fading.
*Spadix shape.*—Columnar, arising from top of peduncle.
*Spadix tip.*—Obtuse.
*Spadix base.*—Obtuse.
*Spadix dimensions.*—Average 6.2 cm in length and 1.7 mm in diameter.
*Spadix color when opening.*—155D to 158D.
*Spadix color when fully opened.*—155D.
*Quantity of flowers per spadix.*—Average 200.
*Spadix flower arrangement.*—Bisexual, rounded.
*Spadix flower dimensions.*—3.5 mm in diameter and 3 mm in depth.
Reproductive organs:
*Anther color.*—155D.
*Amount of pollen.*—Low.
*Pollen color.*—155D.
*Stigma color.*—155D.
*Ovary color.*—155D.
Peduncle:
*Peduncle dimensions.*—Average 55.5 cm in length and 7.0 mm. in diameter.
*Peduncle angle.*—5 degrees from vertical.
*Peduncle color.*—137B to 143A.
*Peduncle strength.*—Strong.
Seed: Seed production has not been observed.
Disease and insect resistance: Plants of the new *Spathiphyllum* have not been observed for disease or insect resistance.

It is claimed:

1. A new and distinct variety of *Spathiphyllum* plant named 'Sweet Silvana' as described and illustrated.

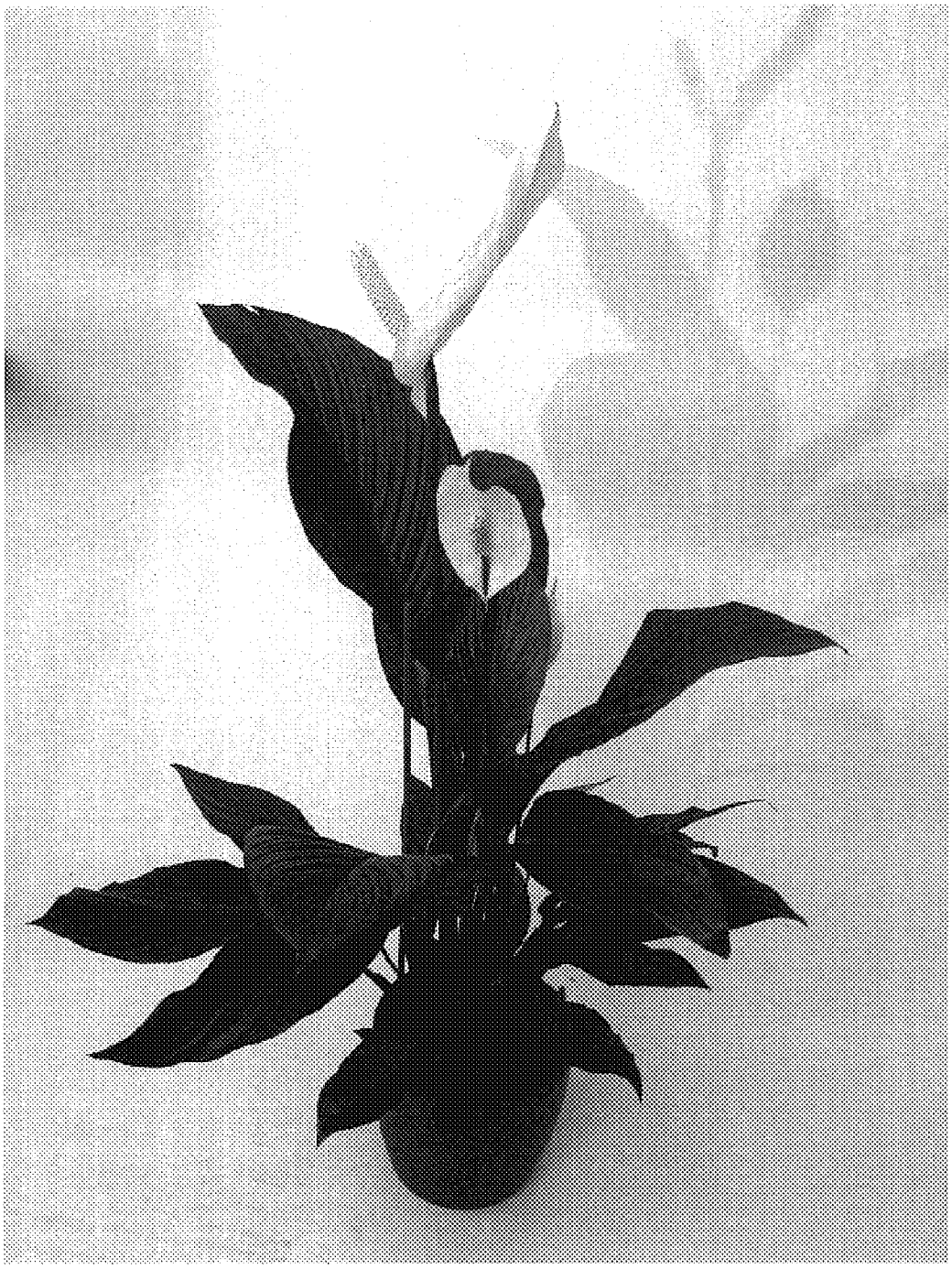

* * * * *